| United States Patent [19] | [11] Patent Number: 5,051,125 |
|---|---|
| Groenwold et al. | [45] Date of Patent: Sep. 24, 1991 |

[54] SYNERGISTIC HERBICIDAL COMPOSITION OF CYCLOATE AND CYANAZINE

[75] Inventors: Bareld E. Groenwold, Los Altos; James L. Ahle, San Jose, both of Calif.

[73] Assignee: ICI Americas Inc., Wilmington, Del.

[21] Appl. No.: 540,956

[22] Filed: Jun. 20, 1990

Related U.S. Application Data

[63] Continuation of Ser. No. 835,904, Mar. 4, 1986, abandoned.

[51] Int. Cl.$^5$ .................... A01N 43/70; A01N 37/22
[52] U.S. Cl. .......................................... 71/93; 71/100; 71/87; 71/88; 71/90; 71/113; 71/118
[58] Field of Search ...................... 71/93, 100, 87, 88, 71/90, 113, 118

[56] References Cited

U.S. PATENT DOCUMENTS

| 3,037,853 | 6/1962 | Luckenbaugh | 71/93 |
|---|---|---|---|
| 3,795,562 | 3/1974 | Lamont et al. | 71/100 |
| 4,009,190 | 2/1977 | Baker | 71/100 |
| 4,021,224 | 5/1977 | Pallos et al. | 71/88 |
| 4,256,481 | 3/1981 | Gardi et al. | 71/88 |
| 4,340,419 | 7/1982 | MacDonald | 71/93 |

FOREIGN PATENT DOCUMENTS

| 1169264 | 6/1984 | Canada . |
|---|---|---|
| 89268 | 3/1983 | European Pat. Off. . |
| 89263 | 9/1983 | European Pat. Off. . |
| 179093 | 2/1978 | Hungary . |
| 181621 | 9/1982 | Hungary . |
| 68-3593 | 6/1967 | South Africa . |
| 69-5397 | 7/1969 | South Africa . |
| 77-3478 | 6/1977 | South Africa . |
| 81-3408 | 7/1982 | South Africa . |
| 813408 | 7/1982 | South Africa . |
| 1271788 | 8/1970 | United Kingdom . |
| 1340271 | 2/1971 | United Kingdom . |
| 1304805 | 4/1971 | United Kingdom . |
| 1450515 | 3/1975 | United Kingdom . |

OTHER PUBLICATIONS

*Pesticide Dictionary*, 1982 (Farm Chemicals Handbook, 1982): pp. C40 and C253.
*Wallace's Farmer*, Dec. 1963, pp. 37 and 43.
Union Carbide Agricultural Products Company brochure: "Wild Proso Millet-It Can Grow You Out of Business."
Anon, Research Disclosures No. 173,34 (1978, C.A. 89, 192373f).
*Wallace's Farmer*, Mar. 1984, p. 26.
Duke et al., Proc. Northeast Weed Science Society, 1972, No. 26, pp. 258, 262.
Globig et al., East German Pat. 211,275; C.A. 102, 742147u (1985).
Farm Chemicals Handbook, 1982 (Farm Chem), pp. C40 and C253.

*Primary Examiner*—Richard L. Raymond
*Assistant Examiner*—B. Bembenick
*Attorney, Agent, or Firm*—Lynn Marcus-Wyner; Joel G. Ackerman

[57] ABSTRACT

A synergistic herbicidal composition with residual activity comprises cycloate and cyanazine in a weight ratio of about 2:1 to 4:1, plus preferably a thiocarbamate herbicide antidote.

28 Claims, No Drawings

SYNERGISTIC HERBICIDAL COMPOSITION OF CYCLOATE AND CYANAZINE

This is a continuation of application Ser. No. 06/835,904, filed Mar. 4, 1986 (now abandoned).

BACKGROUND

This invention pertains to a novel synergistic herbicidal composition which has been found particularly effective in controlling the weed wild proso millet (*Panicum milaceum*).

Wild proso millet is a rapidly spreading grass weed which is difficult to control. It is particularly prevalent in corn and other crops and is found primarily in the upper mid-western states of the United States such as Wisconsin, Minnesota, Iowa, Nebraska and Michigan, adjacent parts of Canada such as Manitoba and Ontario provinces, and in certain portions of Europe, including France, Italy, Austria and the U.S.S.R. This weed has a long germination period, which may be 2-3 months. Many pre-emergent or pre-plant incorporated herbicides utilized in controlling weeds in such crops have an effective activity of less than three months, sometimes by design—to permit quicker biodegradability and less residue in the soil. Consequently, such herbicides may not provide effective control of this weed.

Currently only two registered treatments in the United States provide adequate control of this weed in corn crops. One is a pre-plant incorporated application of the herbicide Eradicane ® (ethyl N,N-di-n-propyl thiocarbamate or EPTC plus the herbicidal antidote N,N-diallyl-2,2-dichloroacetamide) followed by a post-emergence directed application of the herbicide ametryne [2-(ethylamino)-4-isopropyl-amino-6-methylthio-s-triazine]. The other registered treatment is a pre-plant incorporated application of Eradicane ® followed by an early post-emergence application of the combination of pendimethalin [N-(1'-ethylpropyl)-3,4-dimethyl-2,6-dinitrobenzeneamine] together with cyanazine [2-chloro-4-(ethylamino)-6-(2-cyanoisopropylamino)-s-triazine]. In either of these applications, Eradicane ® Extra (which comprises the Eradicane ® formulation plus a herbicide extender) may be substituted for Eradicane ®. The first of these two treatments poses a serious risk of corn injury from ametryne and requires sophisticated equipment; this method therefore is not popular. The second method is expensive and presents a substantial risk of pendimethalin injury to the corn. Furthermore, the latter method does not suppress the production of new weed seeds which contribute to the infestation in subsequent years.

SUMMARY OF THE INVENTION

This invention comprises a novel herbicidal composition which provides excellent residual control of wild proso millet in crops of concern, preferably corn, which composition comprises herbicidally effective amounts of S-ethyl cyclohexylethyl thiocarbamate and 2-chloro-4-(ethylamino)-6-(2-cyanoisopropylamino)-s-triazine, in a weight ratio of from about 2:1 to about 4:1, respectively. In a preferred embodiment the composition also includes a substantially non-phytotoxic, antidotally effective amount of a thiocarbamate herbicide antidote.

The invention also comprises a method for controlling undesirable vegetation in the presence of a crop, particularly a corn crop, by applying to the locus of the crop or undesired vegetation a herbicidal composition comprising herbicidally effective amounts of the two above-mentioned herbicides, in a weight ratio of from about 2:1 to about 4:1, respectively, and, preferably also applying to such locus a substantially non-phytotoxic, antidotally effective amount of a thiocarbamate herbicide antidote.

DETAILED DESCRIPTION AND PRIOR ART

S-Ethyl cyclohexylethyl thiocarbamate is a commercially available herbicide known by the generic names cycloate and hexylthiocarbam. It is primarily sold for use in beets, mainly sugarbeets. This compound will be hereinafter referred to by the name "cycloate". Cycloate has the formula

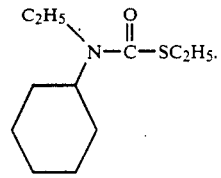

The second compound of this composition, 2-chloro-4-(ethylamino)-6-(2-cyanoisopropylamino)-s-triazine, is a commercial herbicide known by the generic name cyanazine and will be referred to hereinafter by that name. It is sold for use in feed grain crops, including corn and sorghum, and also in crops such as cotton and potatoes. This compound has the formula

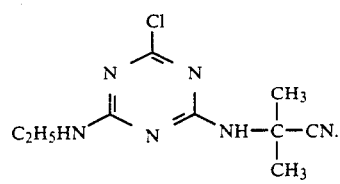

Cycloate can cause substantial injury to certain varieties or strains of corn; consequently for application to corn (unless the variety is one which is resistant to cycloate injury) there must also be used a substantially non-phytotoxic, antidotally effective amount of an antidote which is effective in protecting the corn against injury from thiocarbamate herbicides. The antidote may be physically included in (e.g., mixed with) the cycloate/cyanazine herbicidal composition, or may be separately applied to the same ultimate locus, for instance by seed treatment, soil drenching, in-furrow application or pre-plant incorporation into soil, with the cycloate/cyanazine mixture being separately applied at the same time or subsequently. Wwhen applied as a soil drench, in-furrow or preplant incorporated, the antidote is considered to be a component of the overall composition. The preferred method of application would depend on the specific antidote. Certain antidotes have been found more effective as seed treatments, while others perform best when incorporated into the soil.

A wide range of chemical substances have been found to be effective as thiocarbamate herbicide antidotes, and the preferred compositions of this invention may include any one or more of such antidotes. Some of the more important types of antidotes are amides of haloalkanoic acids, aromatic oxime derivatives, thiazole carboxylic acids and derivatives, and 1,8-naphthalic anhydride.

Amides of haloalkanoic acids have the generalized formula

in which R is a mono- or poly-haloalky group. The halogens may be variously chloro, bromo or iodo; chloro is the preferred halogen, and the preferred group for R in these compounds in general is dichloromethyl, $Cl_2CH-$, i.e., the compounds are amides of dichloroacetic acid. In such compounds the nitrogen is further substituted by at least one other functional group or forms a portion of a heterocyclic ring, as will be described below.

Antidotes of this type are described in a number of publications such as U.S. Pat. Nos. 4,021,224; 4,256,481; and 4,294,764, European Patent Application, Publication No. 104,495, and British Patent 1,521,540. U.S. Pat. No. 4,021,224 contains a broad disclosure of such types of compounds and indicates a great many possibilities for mono- or di-substitution on the nitrogen atom.

One type of antidote disclosed in U.S. Pat. No. 4,021,224 is N,N-diallyl dichloroacetamide,

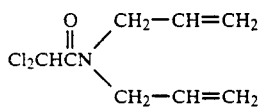

which is generally known commercially as R-25788 and is included as an antidote in several commercial products containing thiocarbamate herbicides.

Another class of haloalkanoic acid amides is that in which the nitrogen atom in the foregoing formula is contained in a heterocyclic ring, for instance an oxazolidine or thiazolidine ring. Preferably R is dichloromethyl, and the preferred compounds have the general formula

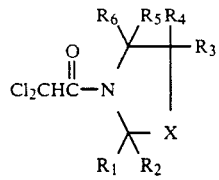

In this formula, X is oxygen or sulfur (preferably oxygen), and $R_1$–$R_6$ are variously independently hydrogen, lower alkyl or phenyl, or $R_1$ and $R_2$ taken together form an alkylene group, preferably a butylene, pentylene or hexylene group, optionally substituted by one or two methyl groups. When X is sulfur, $R_2$ preferably is a group of the general formula $-(CH_2)nCOOZ$ in which Z is an alkyl (preferably lower alkyl), cycloalkyl, cyclohexylmethyl, phenyl, substituted phenyl, benzyl, substituted benzyl, allyl or propargyl group, and n is 0 or 1. Compounds of these types are disclosed for instance in U.S. Pat. Nos. 4,021,224 and 4,256,481 and in European Patent Application (Publication No.) 104,495 (thiazolidines).

Representative compounds of this type include (where not specified, the substituent is hydrogen):

Ozazolidines (X=oxygen)

2,2-dimethyl-N-dichloroacetyl oxazolidine ($R_1$ and $R_2$=methyl);
2,2,5-trimethyl-N-dichloroacetyl oxazolidine ($R_1$, $R_2$ and $R_5$=methyl);
2,2-dimethyl-5-n-propyl-N-dichloroacetyl oxazolidine ($R_1$, $R_2$=methyl, $R_5$=n-propyl);
2,2-dimethyl-5-phenyl-N-dichloroacetyl oxazolidine ($R_1$, $R_2$=methyl, $R_5$=phenyl);
2,2-spirocyclohexyl-N-dichloroacetyl oxazolidine ($R_1$ plus $R_2$ taken together=pentamethylene).

Thiazolidine (X=sulfur)

2-methyl, 2-methylcarboxymethyl-N-dichloroacetyl thiazolidine ($R_1$=methyl, $R_2$=$CH_2COOCH_3$)

Other compounds in which R1 and R2 taken together are alkylene are disclosed for instance in British Patents 1,512,540 and 2,023,582 and Hungarian Patent 181,621.

A third type of haloalkanoic acid amide is disclosed generally in U.S. Pat. No. 4,294,764 and has the general formula

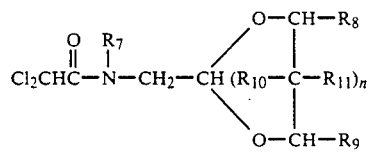

in which $R_7$ may be one of a number of alkyl, alkenyl or alkynyl moieties; $R_8$, $R_9$, $R_{10}$ and $R_{11}$ are independently hydrogen or methyl; and n is 0 or 1. A representative compound of this type is the compound N-(1,3-dioxolan-2-yl-methyl)-N-(2-propenyl)-2,2-dichloroacetamide, which has the formula

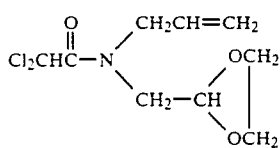

This corresponds to the previous formula in which $R_7$ is 2-propenyl, $R_8$ and $R_9$ are both hydrogen and n is 0.

Oxime derivatives which are suitable for use as antidotes with thiocarbamate herbicides are disclosed, for instance in U.S. Pat. Nos. 4,070,389 and 4,269,775 and have the general formula

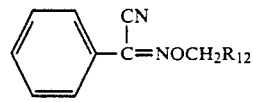

in which $R_{12}$ is cyano or a number of other moieties as indicated in U.S. Pat. No. 4,269,775. Representative compounds of this type are those in which $R_{12}$ is cyano and in which $R_{12}$ is 1,3-dioxolan-2-yl. The latter compound has the chemical name O-[2-(1,3-dioxolanyl)methyl]-alpha-cyanobenzaldoxime.

Thiazole carboxylic acids and derivatives suitable for use as thiocarbamate antidotes are disclosed generally in U.S. Pat. No. 4,199,506 and have the general formula

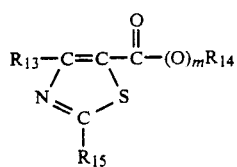

in which $R_{13}$ is alkyl, haloalkyl or trialkoxymethyl; $R_{14}$ is variously hydrogen, agriculturally acceptable cations or various hydrocarbamyl or substituted hydrocarbamyl moieties; and $R_{15}$ is chloro, bromo, iodo, lower alkoxy or substituted or unsubstituted phenoxy. A representative member of this class is the compound benzyl-2-chloro-4-trifluoromethyl-5-thiazole carboxylate ($R_{13}$=trifluoromethyl; $R_{14}$=benzyl, $R_{15}$=chloro; m=1).

The amount of a given antidote to be utilized in combination with the cycloate/cyanazine mixture in the composition of this invention and the manner of its utilization will vary according to the particular antidote to be employed, the crop which is to be protected, the amount or rate of herbicide to be applied, and the soil and climatic conditions of the agricultural environment in which the mixture is to be applied. The selection of a specific antidote for use in the cycloate/cyanazine composition, the manner in which it is to be applied (e.g., tank mix, in-furrow application, seed treatment, etc.), the determination of activity which is nonphytotoxic but antidotally effective, and the amount necessary to provide this result, can be readily performed utilizing the test procedures in the cited patents such as U.S. Pat. No. 4,021,224, in accordance with common practice in the art.

In some cases it may be advantageous to also include in the composition a substance which can provide extension in time of the activity of thiocarbamate herbicides, in an amount effective to extend this activity. Such substances are generally referred to as "thiocarbamate herbicide extenders." A number of substances have been found which possess these properties. Examples of such substances are certain types of organophosphorus compounds, carbamates, and amines, which are disclosed respectively in European Patent Applications publication Nos. 10178, 38945, and 78146 and a number of carbamates, thiocarbamates and dithiocarbamates as disclosed in U.S. patent application Ser. No. 652,710, filed Sept. 19, 1984 of Reed A. Gray et al., assigned to the assignee hereof. These patent applications disclose tests for determining whether a substance has such extending activity, and determining what amount of substance is required in a given case to provide this activity. As with the antidotes, such thiocarbamate herbicide extenders may be physically incorporated into the herbicidal composition or applied separately to the same ultimate locus. Preferred extenders in such compositions are the compound O,O-diethyl-O-phenyl phosphorothioate, disclosed for such use in European Patent Application, Publication No. 10178 and N,N-bis(3-chloroallyl) S-ethyl thiocarbamate, disclosed in the above-mentioned U.S. patent application Ser. No. 652,710.

The herbicidal compositions according to this invention contain the herbicides cycloate and cyanazine in a weight ratio, respectively, of from about 2:1 to about 4:1 (exclusive of auxiliary ingredients). The amount of antidote in the composition (if included) will depend on the particular antidote selected for use, and the rate of application of the cycloate, as well as the crop and climatic conditions to be encountered, and may range from as low as about 0.5 to as high as about 33 percent by weight with respect to cycloate (the corresponding weight ratios of cycloate:antidote are from about 128:1 to about 3:1). If an extender for thiocarbamate herbicides is also included in the composition, the amount of this substance will similarly depend on the extender, crop and conditions, but may generally range from as low as about 2.5 to as high as about 50 percent by weight with respect to cycloate.

HERBICIDAL EVALUATION

Herbicidal evaluations of mixtures of cycloate and cyanazine with various antidotes were conducted in both the greenhouse and in the field.

A. Greenhouse Evaluation—Herbicide Combination

This example demonstrates the synergistic response of combinations of cycloate and cyanazine, in long term or residual control of wild proso millet and two other grassy weeds.

In these tests, three substances were used: cycloate, cyanazine, and the thiocarbamate herbicidal antidote 2,2,5-trimethyl-N-dichloroacetyl oxazolidine. The cycloate was used in the form of an emulsifiable concentrate containing 6 pounds cycloate per gallon and appropriate additives. The cyanazine was used in the form of a wettable powder containing 80% by weight cyanazine, plus diluents and carriers. The antidote was used in the form of an emulsifiable concentrate containing 2 pounds antidote per gallon. Test solutions of the herbicides used in these evaluations were prepared by mixing and addition of appropriate amounts of water to form sprayable solutions or emulsions.

Test flats or pans were filled with virgin sandy loam soil. The treatments to be evaluated were sprayed onto the flats at a rate of 25 gallons/acre (234 liters/hectare) with test compounds being applied at the following rates: cycloate—4 lb/A (4.48 kg/ha); cyanazine—1 lb/A (1.12 kg/ha); oxazolidine antidote—0.17 lb/A (0.19 kg/ha).

After the soil had been sprayed, it was placed in a rotary mixer and mixed or incorporated for a minimum of 3 minutes. After incorporation the soil was placed in the original pans and seeds of three grassy weed species were planted. The weeds were: wild proso millet (*Panicum miliaceum*), shattercane (*Sorghum bicolor*) and giant foxtail (*Setaria faberi*). Only some of the flats containing treated soil were seeded at this time. Other flats containing the treated soil were similarly seeded at intervals of 3, 6 and 9 weeks after spraying of the herbicides, in order to test for residual control by the test compounds. After seeding, the test flats were placed in a greenhouse at a temperature of approximately 70°-80° F. (21°-27° C.) and watered by sprinkling. At dates approximately 3 weeks after seeding, the degree of injury or control of the weeds was determined by visual comparison of untreated check flats seeded at the same time. The injury rating, on a scale of 0 to 100%, was recorded for each species as percent control, with 0% representing no injury and 100% representing complete kill. The results of these tests are contained in the following Table I. Under the heading "O" are given the ratings for the individual herbicides or mixtures as observed. Under the heading "E" are provided the expected results for combinations of the two herbicides, based on the response for each herbicide alone, derived from this data using Limpel's formula, namely:

$$E = X + Y - \frac{XY}{100}$$

where

X = the observed percent injury when one of the herbicides is used alone and
Y = the observed percent injury when the other herbicide is used alone.

This formula is contained in the article "Weed Control by Dimethylchloroterephthalate Alone and in Certain Combination," Limpel et al., *Proc. NEWCC.*, Vol. 16, pp. 48–53 (1962). When the observed result exceeds the result which would have been expected using this formula, synergism is demonstrated.

The ratings are indicated as being taken at times $T_1$–$T_4$. These correspond to dating and evaluation days over the period of the tests as follows:
$T_1$—seeded on day 0, rated on day 20
$T_2$—seeded on day 21, rated on day 41
$T_3$—seeded on day 43, rated on day 63
$T_4$—seeded on day 64, rated on day 84

TABLE I

| Application Rates: | Cycloate | | | | 4 lb/acre | | | |
| | Oxazolidine antidote | | | | 0.17 lb/acre | | | |
| | cyanazine | | | | 1 lb/acre | | | |
| | $T_1$ | | $T_2$ | | $T_3$ | | $T_4$ | |
| Herbicide | O | E | O | E | O | E | O | E |
| Wild Proso Millet - % Control | | | | | | | | |
| cycloate + antidote | 100 | | 97 | | 30 | | 27 | |
| cyanazine | 73 | | 63 | | 30 | | 37 | |
| cycloate + cyanazine + antidote | 99 | 100 | 100 | 99 | 88* | 51 | 67* | 54 |
| Shattercane - % Control | | | | | | | | |
| cycloate + antidote | 63 | | 60 | | 3 | | 0 | |
| cyanazine | 83 | | 92 | | 67 | | 40 | |
| cycloate + cyanazine + antidote | 94 | 94 | 99 | 97 | 93* | 68 | 93* | 40 |
| Giant Foxtail - % Control | | | | | | | | |
| cycloate + antidote | 100 | | 93 | | 94 | | 77 | |
| cyanazine | 100 | | 100 | | 88 | | 77 | |
| cycloate + cyanazine + antidote | 100 | 100 | 100 | 100 | 99 | 96 | 100 | 95 |

*Synergism demonstrated.

As shown by the data in this table, cyanazine and cycloate alone, as well as the mixture of the two, maintained the initial control of the weeds through the first six weeks after application. However, 9 weeks after initial incorporation into the soil, the activity of the individual herbicides against shattercane and wild proso millet began to fall off markedly. The activity of the combination was expected to similarly decline. However, in fact, the combination of cycloate plus cyanazine at the indicated ratios still provided surprisingly quite good control of all three weeds.

Greenhouse Evaluations With Various Herbicidal Antidotes

Mixtures of cycloate and cyanazine with a number of different thiocarbamate herbicide antidotes were prepared and evaluated. As before, simultaneous evaluations were conducted using cycloate and cyanazine alone for comparison. The test procedure was as follows.

(a) Pre-plant Incorporation of Herbicides With Antidotes

Test flats were filled with moist, virgin sandy loam soil, and 17-17-17 fertilizer was added. The flats were then sprayed on a linear spray table at a volume of 25 gallons/acre (234 lit/ha) with the test herbicides, at application rates as given below. Immediately after spraying, the soil from all the flats was placed in a rotary mixer and mixed for at least three minutes. After incorporation the soil was placed in storage containers. The next day, some of the soil was placed in test flats, which were seeded with two varieties of corn and four grassy weeds. The corn varieties utilized were Dekalb XL-43a and XL-67. The weeds were Fall panicum (*Panicum dichotomiflorum*) (first and third plantings), velvetleaf (*Abutilon theophrasti*) (second planting only), shattercane, giant foxtail and wild proso millet.

At intervals of 3, 6, and 9 weeks after spraying, additional soil samples were placed in flats and seeded with seeds of the same species as previously. After seeding, the flats were placed in a greenhouse at a temperature of 70°–80° F. (21°–27° C.) and watered by sprinkling. Between plantings, the unused soil was kept in the greenhouse at temperatures of 70°–80° F. (21°–27° C.).

Each flat was checked for degree of injury or control of weeds approximately 3 weeks after seeding, by comparing it with untreated check flats of the same age. The injury rating, on a scale of 0 to 100%, was recorded for each species as percent control, with 0% representing no injury and 100% representing complete control.

The results of these tests are given in Table II below. Under the heading "O" are given the ratings for the compounds applied as observed. Under the heading "E" are provided the expected results for combinations of the two herbicides, using Limpel's formula.

The herbicides were prepared in solution form and applied as follows. Cycloate was utilized in the form of an emulsifiable concentrate containing approximately 75.3 weight percent cycloate, and was mixed with water to produce a sprayable emulsion. Cyanazine was employed in the form of a wettable powder containing approximately 80% by weight of the herbicide, and was mixed with water to form a sprayable solution. Antidotes were employed as technical grade material, with appropriate amounts of material being added to provide application rates as given below.

The test compounds were sprayed on the flats at the following application rates:
cycloate—4 lb/A (4.48 kg/ha)
cyanazine—1 lb/A (1.12 kg/ha)
antidotes—0.33 lb/A (0.37 kg/ha)

(b) Pre-plant Incorportion and Seed Treatment With Antidotes

In a second series of tests, the antidotes were incorporated by seed treatment in an amount of 0.5% by weight of the antidote based on the weight of the seed. In such a treatment, 10 g of the corn seed was mixed with 50 mg of the specified antidote and 1 or 2 drops of methanol were added to assist the antidote in adhering to the seeds. The herbicides were applied in the same manner and at the same application rates as before.

Six different antidotes were utilized in these tests, and are indicated in Table II by the following reference numbers:

| Antidotes | |
|---|---|
| Compound Name | Number |
| N,N-diallyl dichloroacetamide (R-25788) | 1 |
| 2,2,5-trimethyl-N-dichloroacetyl oxazolidine | 2 |
| 2,2-spirocyclohexyl-N-dichloroacetyl oxazolidine | 3 |
| N-(1,3-dioxolan-2-ylmethyl)-N-(2-propenyl)-2,2-dichloroacetamide | 4 |
| O-[2-(1,3-dioxolanyl)methyl]-alpha-cyanobenzaldoxime | 5 |
| 1,8-naphthalic anhydride | 6 |

Table II contains the results of the four plantings and evaluations which occurred as follows:
first planting—seeded on day 1, evaluated on day 20
second planting—seeded on day 22, evaluated on day 41
third planting—seeded on day 42, evaluated on day 63
fourth planting—seeded on day 64, evaluated on day 84

"fourth planting" evaluation (12 weeks after application), weed control had decreased quite sharply in general, but combinations of cycloate with cyanazine were still showing far better activity than expected against the proso millet. A fifth planting and evaluation was carried out, but there was virtually no weed control by any test composition.

As part of this series of tests, evaluation was also made of the injury, if any, to the corn varieties. The results, for the first three plantings, are shown in Table III below. No injury was observed for any test compositions in the fourth or fifth plantings.

TABLE III

| | | % Injury to Corn Varieties | | | | | |
|---|---|---|---|---|---|---|---|
| | | First Planting | | Second Planting | | Third Planting | |
| Herbicide | Number | XL-43a | XL-67 | XL-43a | XL-67 | XL-43a | XL-67 |
| cycloate | — | 50 | 90 | 20 | 98 | 0 | 15 |
| cyanazine | — | 0 | 0 | 0 | 5 | 0 | 0 |
| cycloate + cyanazine | — | 55 | 90 | 0 | 70 | 0 | 5 |
| cycloate + cyanazine | 1 | 0 | 0 | 0 | 0 | 0 | 0 |
| cycloate + cyanazine | 2 | 0 | 0 | 0 | 0 | 0 | 0 |
| cycloate + cyanazine | 3 | 0 | 50 | 0 | 50 | 0 | 0 |
| cycloate + cyanazine | 4 | 0 | 40 | 0 | 50 | 0 | 0 |
| cycloate + cyanazine | 5 | 0 | 55 | 0 | 35 | 0 | 0 |
| cycloate + cyanazine | 6 | 70 | 85 | 5 | 35 | 0 | 0 |
| Seed Treatment with Antidote | | | | | | | |
| cycloate + cyanazine | 1 | 0 | 5 | 0 | 0 | 0 | 5 |
| cycloate + cyanazine | 2 | 0 | 0 | 0 | 0 | 0 | 15 |
| cycloate + cyanazine | 3 | 0 | 20 | 0 | 0 | 0 | 25 |
| cycloate + cyanazine | 4 | 0 | 5 | 0 | 0 | 0 | 5 |
| cycloate + cyanazine | 5 | 5 | 0 | 0 | 0 | 0 | 5 |
| cycloate + cyanazine | 6 | 0 | 30 | 5 | 5 | 0 | 0 |

The information in Table III demonstrates that while cycloate itself, and cycloate in mixtures with cyanazine, can cause injury to corn for at least three weeks (and up to six weeks for a sensitive variety such as XL-67) typical thiocarbamate antidotes function effectively, when properly applied, to protect corn from such injury. The

TABLE II

| | | First Planting % Control | | | | Second Planting % Control | | | | Third Planting % Control | | | | Fourth Planting % Control | | | |
|---|---|---|---|---|---|---|---|---|---|---|---|---|---|---|---|---|---|
| | | Wild Proso Millet | | Other weeds (avg.)* | | Wild Proso Millet | | Other weeds (avg.) | | Wild Proso Millet | | Other weeds (avg.) | | Wild Proso MIllet | | Other weeds (avg.) | |
| Herbicide | Antidote Number | O | E | O | E | O | E | O | E | O | E | O | E | O | E | O | E |
| cycloate | — | 100 | | 100 | | 80 | | 97 | | 45 | | 22 | | 10 | | 10 | |
| cyanazine | — | 55 | | 90 | | 40 | | 70 | | 35 | | 47 | | 0 | | 10 | |
| cycloate + cyanazine | — | 99 | 100 | 100 | 100 | 94 | 88 | 100 | 100 | 75 | 64 | 90 | 59 | 45 | 10 | 20 | 19 |
| cycloate + cyanazine | 1 | 100 | 100 | 100 | 100 | 97 | 88 | 99 | 100 | 75 | 64 | 89 | 59 | 35 | 10 | 30 | 19 |
| cycloate + cyanazine | 2 | 100 | 100 | 95 | 100 | 85 | 88 | 82 | 100 | 80 | 64 | 80 | 59 | 30 | 10 | 15 | 19 |
| cycloate + cyanazine | 3 | 99 | 100 | 100 | 100 | 97 | 88 | 100 | 100 | 80 | 64 | 89 | 59 | 30 | 10 | 20 | 19 |
| cycloate + cyanazine | 4 | 100 | 100 | 97 | 100 | 94 | 88 | 88 | 100 | 65 | 64 | 85 | 59 | 40 | 10 | 20 | 19 |
| cycloate + cyanazine | 5 | 99 | 100 | 98 | 100 | 92 | 88 | 92 | 100 | 65 | 64 | 75 | 59 | 40 | 10 | 25 | 19 |
| cycloate + cyanazine | 6 | 100 | 100 | 99 | 100 | 94 | 88 | 99 | 100 | 75 | 64 | 85 | 59 | 35 | 10 | 20 | 19 |
| Seed Treatment with Antidote | | | | | | | | | | | | | | | | | |
| cycloate + cyanazine | 1 | 100 | 100 | 98 | 100 | 98 | 88 | 99 | 100 | 75 | 64 | 93 | 59 | 35 | 10 | 25 | 19 |
| cycloate + cyanazine | 2 | 100 | 100 | 94 | 100 | 85 | 88 | 87 | 100 | 70 | 64 | 88 | 59 | 30 | 10 | 23 | 19 |
| cycloate + cyanazine | 3 | 100 | 100 | 99 | 100 | 93 | 88 | 99 | 100 | 80 | 64 | 93 | 59 | 40 | 10 | 30 | 19 |
| cycloate + cyanazine | 4 | 100 | 100 | 96 | 100 | 88 | 88 | 95 | 100 | 80 | 64 | 91 | 59 | 40 | 10 | 23 | 19 |
| cycloate + cyanazine | 5 | 98 | 100 | 98 | 100 | 90 | 88 | 99 | 100 | 75 | 64 | 92 | 59 | 35 | 10 | 20 | 19 |
| cycloate + cyanazine | 6 | 99 | 100 | 99 | 100 | 93 | 88 | 99 | 100 | 75 | 64 | 88 | 59 | 30 | 10 | 17 | 19 |

*Average of shattercane and giant foxtail only; panicum did not germinate sufficiently.

As can be seen from the data in Table II, at the end of 6 weeks ("second planting" evaluation), the mixture of cycloate+cyanazine was demonstrating activity against wild proso millet as expected or somewhat better than expected. At the end of 9 weeks from application ("third planting" evaluation) unexpected activity was clearly demonstrated not only in the case of wild proso millet, but also for the overall control of other weeds in this test, particularly shattercane. In the activity pattern of antidotes 3-6 in protecting corn from thiocarbamate herbicidal injury is consistent with their expected performance—they are generally employed as seed treatments rather than by pre-plant incorporation into soil.

(b) Pre-Plant Incorporation; use of herbicide extender

The test procedure was as in series (a). Weeds employed were shattercane, giant foxtail, velvetleaf and wild proso millet. Cyanazine was used in the form of a wettable powder containing approximately 80% by weight cyanazine. Cycloate was used primarily in the form of an emulsifiable concentrate containing approximately 75.3 weight percent cycloate and also in two different microencapsulated compositions—compositions E, H and I which included oil and compositions J and K which did not. Antidote 1 was employed in this series of tests. When used with a cycloate emulsifiable concentrate it was employed as in series (a); it was physically incorporated into the microencapsulated formulations.

The thiocarbamate herbicide extender was O,O-diethyl-phenyl phosphorothioate.

cycloate—4 lb/acre (4.48 kg/ha)
cyanazine—1 lb/acre (1.12 kg/ha) and 2 lb/acre (2.24 kg/ha)
antidote—0.33 lb/acre (0.37 kg/ha)
extender—1 lb/acre (1.12 kg/ha)

The results of these tests are included in Table IV. Plantings and evaluations were as follows:
First planting—seeded on day 1, evaluated on day 21;
Second planting—seeded on day 22, evaluated on day 42;
Third planting—seeded on day 42; evaluated on day 62;
Fourth planting—seeded on day 63; evaluated on date 85;
Fifth planting—seeded on day 86; evaluated on day 115.

TABLE IV

| | | First Planting % Control | | | | Second Planting % Control | | | | Third Planting % Control | | | |
|---|---|---|---|---|---|---|---|---|---|---|---|---|---|
| | | Wild Proso Millet | | Other weeds (avg.) | | Wild Proso Millet | | Other weeds (avg.) | | Wild Proso Millet | | Other weeds (avg.) | |
| Test Composition | Antidote | O | E | O | E | O | E | O | E | O | E | O | E |
| A: cycloate | | 97 | | 99 | | 95 | | 99 | | 40 | | 83 | |
| B: cyanazine | | 53 | | 93 | | 43 | | 86 | | 17 | | 69 | |
| C: cyanazine* | | 83 | | 99 | | 63 | | 92 | | 27 | | 83 | |
| D: cycloate + cyanazine + antidote 1 | | 100 | 99 | 100 | 100 | 97 | 97 | 100 | 100 | 67 | 50 | 98 | 95 |
| E: cycloate + cyanazine* + antidote 1 | | 100 | 99 | 100 | 100 | 97 | 98 | 99 | 100 | 98 | 56 | 98 | 97 |
| F: cycloate + extender + antidote 1 | | 98 | | 98 | | 94 | | 98 | | 73 | | 93 | |
| G: cycloate + cyanazine + extender + antidote 1 | | 100 | 100 | 100 | 100 | 96 | 97 | 100 | 100 | 77 | 78 | 100 | 98 |
| H: cycloate + antidote 1** | | 98 | | 97 | | 94 | | 99 | | 63 | | 89 | |
| I: cycloate + cyanazine + antidote 1** | | 99 | 99 | 100 | 100 | 99 | 97 | 100 | 100 | 77 | 74 | 96 | 97 |
| J: cycloate + antidote 1*** | | 99 | | 99 | | 97 | | 99 | | 70 | | 84 | |
| K: cycloate + antidote 1*** | | 99 | 100 | 100 | 100 | 99 | 99 | 100 | 100 | 70 | 82 | 98 | 96 |

*cyanazine application rate 2 lb/acre
**microencapsulated, plus oil
***microencapsulated, no oil Table V below shows injury (if any) to the two varieties of corn included in the tests, in the first through third plantings. In the fourth and fifth plantings, no injury on corn was observed except that the extender composition G caused approximately 20% injury to the XL-67 variety. This is consistent with the general extension of herbicidal activity of cycloate.

The test compositions are as in Table IV above.

TABLE V

| Test Composition | % Injury | | | | | |
|---|---|---|---|---|---|---|
| | First Planting | | Second Planting | | Third Planting | |
| | XL-43a | XL-67 | XL-43a | XL-67 | XL-43a | XL-67 |
| A | 77 | 90 | 13 | 80 | 0 | 67 |
| B | 10 | 10 | 0 | 0 | 0 | 0 |
| C | 17 | 17 | 22 | 7 | 3 | 0 |
| D | 3 | 63 | 0 | 43 | 0 | 7 |
| E | 13 | 73 | 0 | 40 | 0 | 27 |
| F | 0 | 33 | 0 | 27 | 0 | 10 |
| G | 3 | 17 | 0 | 43 | 0 | 20 |
| H | 0 | 67 | 0 | 17 | 0 | 3 |
| I | 3 | 33 | 0 | 43 | 0 | 23 |
| J | 0 | 70 | 0 | 27 | 0 | 7 |
| K | 3 | 73 | 0 | 43 | 0 | 10 |

When the information in Table IV is compared with that in Table II, the unexpected continued (residual) activity of mixtures of cycloate and cyanazine after 6-9 weeks (third planting) is clearly demonstrated. As seen from table IV, the inclusion of a thiocarbamate herbicidal extender produces an overall extension of the cycloate activity so that the unexpected residual activity is first demonstrated three weeks later, in the fourth planting.

Field Evaluations

Mixtures of cycloate and cyanazine were evaluated for residual control of wild proso millet in three fields in Wisconsin. Field No. 1 had a loamy soil, and a moderate but uniform stand of wild proso millet, Field Nos. 2 and 3 had fine sandy loam soil and a heavy uniform infestation of wild proso millet. The herbicides in the test were incorporated by pre-plant incorporation with a sprayer followed by discing. Three replications were performed with each herbicidal treatment. At the end of 12 weeks, the tests were evaluated for control of wild proso millet, in terms of percent control from 0 to 100% by comparison by with an untreated check plot.

The other herbicides tested were cycloate, cycloate with antidote No. 2 of Table II, and cycloate with said antidote and cyanazine. The cycloate was variously utilized in two different forms: an emulsifiable concentrate containing 6 pounds cycloate per gallon, and a microencapsulated form containing 4 pounds cycloate per gallon. The antidote was used in the form of an emulsifiable concentrate containing 2 pounds antidote per gallon. The cyanazine was used in the form of a wettable powder containing 80% by weight cyanazine. The various compositions were prepared by standard tank mixing techniques using the above mentioned materials. The cycloate was applied at rates of 4 and 6 pounds per acre; the cyanazine at a rate of 2 lb/A; the antidote at a rate of 0.7 lb/A.

The results of these tests are shown in the following Table VI.

TABLE VI

| | | FIELD EVALUATIONS | | | |
|---|---|---|---|---|---|
| Test No. | Herbicide | Herbicide Application Rate (lb/A) | Wild Proso Millet - % Control | | |
| | | | Field #1 | Field #2 | Field #3 |
| 1 | cycloate | 4 | 90 | 78 | 67 |
| 2 | cycloate antidote #2 | 4 | 77 | 83 | 75 |
| 3 | cycloate* antidote #2 | 4 | 72 | 78 | 63 |
| 4 | cycloate antidote #2 cyanazine | 4  2 | 90 | 85 | 72 |
| 5 | cycloate | 6 | 93 | 85 | 82 |
| 6 | cycloate antidote #2 | 6 | 90 | 92 | 78 |
| 7 | cycloate* antidote #2 | 6 | 88 | 90 | 83 |
| 8 | cycloate antidote #2 cyanazin | 6  2 | 90 | 93 | 82 |

*in microencapsulated form

These evaluations demonstrate the long-term residual control using mixtures of cycloate and cyanazine at weight ratios (based on application rates) of 2:1 and 3:1.

Cycloate is generally sold in one of two physical forms: an emulsifiable concentrate and a granular form. Cyanazine is generally marketed in the form of a wettable powder, and has also been commercially available as granules, an emulsifiable concentrate, or a suspension concentrate. Cycloate itself is a liquid; cyanazine a solid.

In any event, compositions containing the two herbicides, together with an antidote and other optional additives such as an extender may be prepared in a number of conventional ways.

The two herbicides, in technical grade, may be mixed and formulated for instance as a flowable composition or as a granule containing the mixture, together with an appropriate antidote and extender, if desirable.

Alternatively, the two herbicides may be obtained in their commercially available forms, and combined in a tank mix for application to a field. For instance, cycloate in the form of an emulsifiable concentrate may be mixed with water and cyanazine in the form of a wettable powder, to form a sprayable suspension or solution, which may be further diluted with water if desired. The antidote, when used, may be included in said suspension or solution, or may be separately applied, as by seed treatment. The amounts of formulated cycloate and cyanazine, and water, are selected so as to provide solutions containing the desired weight ratio of cycloate to cyanazine, and for application to the field at the desired rate. Specific examples of compositions containing the two herbicides, with antidotes, are contained in the foregoing evaluation descriptions.

What is claimed is:

1. A herbicidal composition comprising herbicidally effective amounts of S-ethyl cyclohexylethyl thiocarbamate and 2-chloro-4-(ethylamino)-6-(2-cyanoisopropylamino)-s-triazine, in a weight ratio of about 2:1 to about 4:1.

2. A composition according to claim 1 further comprising a substantially non-phytotoxic, antidotally effective amount of a thiocarbamate herbicide antidote.

3. A composition according to claim 2 in which the antidote is an amide of a haloalkanoic acid, an aromatic oxime derivative, a thiazole carboxylic acid or derivative thereof, or 1,8-naphthalic anhydride.

4. A composition according to claim 2 in which the antidote is an amide of a haloalkanoic acid.

5. A composition according to claim 4 in which the antidote is an amide of dichloroacetic acid.

6. A composition according to claim 5 in which the antidote is N,N-diallyl dichloroacetamide.

7. A composition according to claim 5 in which the antidote is an oxazolidine having the formula

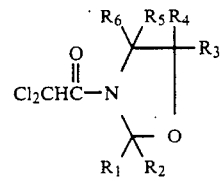

in which $R_1$, $R_2$, $R_3$, $R_4$, $R_5$ and $R_6$ are independently hydrogen, lower alkyl or phenyl, or $R_1$ and $R_2$ taken together form an alkylene ring together with the carbon atom of the oxazolidine ring to which they are bonded.

8. A composition according to claim 7 in which $R_1$, $R_2$ and $R_5$ are each methyl and $R_3$, $R_4$ and $R_6$ are each hydrogen.

9. A composition according to claim 4 in which the antidote has the formula

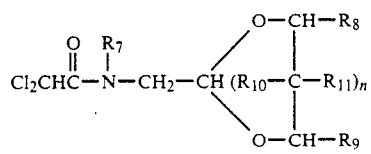

in which $R_7$ is alkyl, alkenyl or alkynyl; $R_8$, $R_9$, $R_{10}$ and $R_{11}$ are independently hydrogen or methyl; and n is 0 or 1.

10. A composition according to claim 9 in which the antidote has the formula

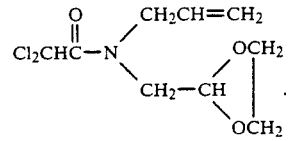

11. A composition according to claim 1 further comprising an amount of an thiocarbamate herbicide extender effective to extend the soil life of the thiocarbamate.

12. A composition according to claim 11 wherein the extender is O,O-diethyl-O-phenyl phosphorothioate.

13. A method of controlling undesirable vegetation in the presence of a crop comprising applying to the locus of said vegetation or said crop a herbicidal composition comprising herbicidally effective amounts of S-ethyl cyclohexylethyl thiocarbamate and 2-chloro-4-(ethylamino)-6-(2-cyanoisopropylamino)-s-triazine in a weight ratio of about 2:1 to about 4:1.

14. A method according to claim 13 further comprising applying to said locus a substantially nonphytotoxic, antidotally effective amount of a thiocarbamate herbicide antidote.

15. A method according to claim 14 in which the crop is corn.

16. A method according to claim 14 in which the thiocarbamate, the triazine and the antidote are first combined into a composition and the composition is applied to the locus.

17. A method according to claim 14 in which the thiocarbamate and triazine are first combined into a composition which is applied to the locus and the antidote is separately applied to the locus.

18. A method according to claim 14 in which the antidote is applied as a seed treatment for the crop seed prior to planting.

19. A method according to claim 14 in which the antidote is an amide of a haloalkanoic acid, an aromatic oxime derivative, a thiazole carboxylic acid or derivative thereof, or 1,8-naphthalic anhydride.

20. A method according to claim 14 in which the antidote is an amide of a haloalkanoic acid.

21. A method according to claim 20 in which the antidote is an amide of dichloroacetic acid.

22. A method according to claim 21 in which the antidote is N,N-diallyl dichloroacetamide.

23. A method according to claim 21 in which the antidote is an oxazolidine having the formula

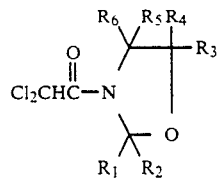

in which $R_1$, $R_2$, $R_3$, $R_4$, $R_5$ and $R_6$ are independently hydrogen, lower alkyl or phenyl, or $R_1$ and $R_2$ taken together form an alkylene ring together with the carbon atom of the oxazolidine ring to which they are bonded.

24. A method according to claim 23 in which $R_1$, $R_2$ and $R_5$ are each methyl and $R_3$, $R_4$ and $R_6$ are each hydrogen.

25. A method according to claim 20 in which the antidote has the formula

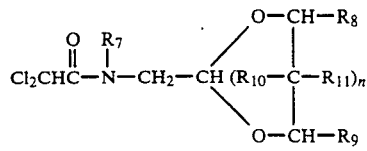

in which $R_7$ is alkyl, alkenyl or alkynyl; $R_8$, $R_9$, $R_{10}$ and $R_{11}$ are independently hydrogen or methyl; and n is 0 or 1.

26. A method according to claim 25 in which the antidote has the formula

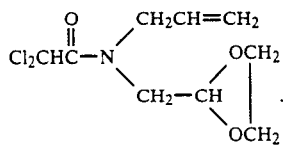

27. A method according to claim 13 further comprising applying to said locus an amount of a thiocarbamate herbicide extender effective to extend the soil life of the thiocarbamate herbicide.

28. A method according to claim 27 wherein the extender is O,O-diethyl-O-phenyl phosphorothioate.

* * * * *